(12) United States Patent
Griess et al.

(10) Patent No.: US 8,218,810 B1
(45) Date of Patent: Jul. 10, 2012

(54) SIGNALING DEVICE

(75) Inventors: Herbert C. Griess, Lincoln, NE (US); Thomas A. Murray, Plantation, FL (US); Eugene I. Nosov, Omaha, NE (US)

(73) Assignee: Stanley Security Solutions, Inc., Indianapolis, IN (US)

( * ) Notice: Subject to any disclaimer, the term of this patent is extended or adjusted under 35 U.S.C. 154(b) by 1343 days.

(21) Appl. No.: 11/780,305

(22) Filed: Jul. 19, 2007

Related U.S. Application Data (60) Provisional application No. 60/831,783, filed on Jul. 19, 2006.

(51) Int. Cl.
*G06K 9/00* (2006.01)
*G08B 23/00* (2006.01)

(52) U.S. Cl. .................................... 382/100; 340/573.4

(58) Field of Classification Search ........... 382/100–322
See application file for complete search history.

(56) References Cited

U.S. PATENT DOCUMENTS

| | | | |
|---|---|---|---|
| 3,624,494 A | 11/1971 | Turan | |
| 4,095,214 A | 6/1978 | Minasy | |
| 4,223,830 A | 9/1980 | Walton | |
| 4,682,155 A | 7/1987 | Shirley | |
| 4,885,571 A | 12/1989 | Pauley et al. | |
| 4,952,913 A | 8/1990 | Pauley et al. | |
| 5,025,486 A | 6/1991 | Klughart | |
| 5,051,727 A | 9/1991 | Fockens | |
| 5,057,824 A | 10/1991 | Stokes | |
| 5,179,421 A * | 1/1993 | Parker et al. | 356/139.06 |
| 5,268,670 A | 12/1993 | Brasch et al. | |
| 5,268,734 A * | 12/1993 | Parker et al. | 356/139.06 |
| 5,298,884 A * | 3/1994 | Gilmore et al. | 340/573.4 |
| 5,494,046 A | 2/1996 | Cross | |
| 5,602,535 A | 2/1997 | Boyles et al. | |
| 5,627,520 A * | 5/1997 | Grubbs et al. | 340/572.1 |
| 5,680,106 A | 10/1997 | Schrott et al. | |
| 5,812,065 A | 9/1998 | Schrott et al. | |
| 5,883,576 A * | 3/1999 | De La Huerga | 340/573.1 |
| 6,054,928 A * | 4/2000 | Lemelson et al. | 340/573.4 |
| 6,108,377 A | 8/2000 | Sass et al. | |
| 6,130,620 A * | 10/2000 | Pinnow et al. | 340/5.86 |
| 6,181,253 B1 * | 1/2001 | Eschenbach et al. | 340/573.4 |
| 6,262,666 B1 * | 7/2001 | Lodichand | 340/573.1 |
| 6,489,893 B1 * | 12/2002 | Richards et al. | 340/573.4 |
| 6,492,906 B1 * | 12/2002 | Richards et al. | 340/573.4 |
| 6,535,108 B1 | 3/2003 | Schrott et al. | |
| 6,674,368 B2 * | 1/2004 | Hawkins et al. | 340/573.4 |
| 7,106,197 B2 * | 9/2006 | Gaiotto et al. | 340/572.1 |
| 7,132,944 B1 * | 11/2006 | Kron et al. | 340/572.1 |
| 7,248,840 B2 * | 7/2007 | Chien | 455/95 |
| 7,317,382 B2 * | 1/2008 | Pratt et al. | 340/428 |
| 7,936,262 B2 * | 5/2011 | Derrick et al. | 340/539.13 |
| 8,022,982 B2 * | 9/2011 | Thorn | 348/78 |
| 8,031,077 B2 * | 10/2011 | Derrick et al. | 340/573.1 |
| 2003/0174059 A1 * | 9/2003 | Reeves | 340/573.4 |
| 2005/0024203 A1 * | 2/2005 | Wolfe | 340/539.22 |

(Continued)

*Primary Examiner* — Manav Seth
(74) *Attorney, Agent, or Firm* — Faegre Baker Daniels LLP (57) ABSTRACT

A signaling device is disclosed that transmits a signal to a personal monitoring system. The signaling device may include an array of RLC components that determine the frequency of the signaling device. The frequency may be tuned by adding or removing RLC components from impacting the frequency. The signaling device may also include a wake-up mechanism for activating the signaling device for normal use and a signal indicating that a predetermined useful life is about to end.

13 Claims, 4 Drawing Sheets

U.S. PATENT DOCUMENTS

| | | | |
|---|---|---|---|
| 2005/0052282 A1* | 3/2005 | Rodgers et al. | 340/572.1 |
| 2005/0128096 A1* | 6/2005 | Adams | 340/686.1 |
| 2005/0146434 A1* | 7/2005 | Gaiotto et al. | 340/568.2 |
| 2005/0148828 A1* | 7/2005 | Lindsay | 600/300 |
| 2006/0025897 A1* | 2/2006 | Shostak et al. | 701/1 |
| 2006/0047187 A1* | 3/2006 | Goyal et al. | 600/300 |
| 2006/0139168 A1* | 6/2006 | Pratt et al. | 340/539.22 |
| 2006/0195261 A1* | 8/2006 | Riley | 701/213 |
| 2006/0261931 A1* | 11/2006 | Cheng | 340/426.1 |
| 2007/0222588 A1* | 9/2007 | Wolfe | 340/539.13 |
| 2008/0055408 A1* | 3/2008 | Wun | 348/122 |
| 2008/0094212 A1* | 4/2008 | Breed | 340/541 |
| 2009/0043441 A1* | 2/2009 | Breed | 701/29 |
| 2009/0212967 A1* | 8/2009 | Bonasia et al. | 340/825.22 |

* cited by examiner

SIGNALING DEVICE

RELATED APPLICATIONS

The present application claims priority to U.S. Provisional Patent Application Ser. No. 60/831,783, titled "Signaling Device," to Griess et al, filed Jul. 19, 2006, the disclosure of which is expressly incorporated by reference herein.

BACKGROUND AND SUMMARY OF THE INVENTION

The present invention relates generally to signaling devices. More particularly, the present invention relates to signaling devices worn by patients to prevent unauthorized exiting from a facility, such as a care facility.

According to one aspect of the present disclosure, a signaling device assembly is provided that includes a package including an interior region and a signaling device for use with a personal monitoring system that detects the location of a person wearing the signaling device. The signaling device is positioned in the interior region of the package and includes a housing, a control circuit, and non-intrusive means for changing the mode of the control circuit.

According to another aspect of the present disclosure, a method of enabling a signaling device for use with a personal monitoring system that detects the location of a person wearing the signaling device is provided. The method includes the steps of providing a signaling device configured to communicate with the personal monitoring system. The signaling device has a sleep mode and an active mode. The method further includes the step of automatically changing the mode of the signaling device from the sleep mode to the active mode to enable the signaling device.

According to another aspect of the present disclosure, a signaling device is provided for use with a personal monitoring system that detects the location of a person wearing the signaling device. The signaling device includes a housing, a control circuit supported by the housing, and a communicator supported by the housing and configured to communicate with the personal monitoring system. The control circuit monitors a predetermined useful life of the signaling device and instructs the communicator to send a signal indicating the end of the useful life is approaching.

Additional features of the present invention will become apparent to those skilled in the art upon consideration of the following detailed description of the presently perceived best mode of carrying out the invention.

BRIEF DESCRIPTION OF THE DRAWINGS

The detailed description of the drawings particularly refers to the accompanying figures in which.

DETAILED DESCRIPTION OF ILLUSTRATIVE EMBODIMENTS

The embodiments disclosed below are not intended to be exhaustive or to limit the invention to the precise forms disclosed in the following detailed description. Rather, the embodiments are chosen and described so that others skilled in the art may utilize their teachings.

Figure 1:
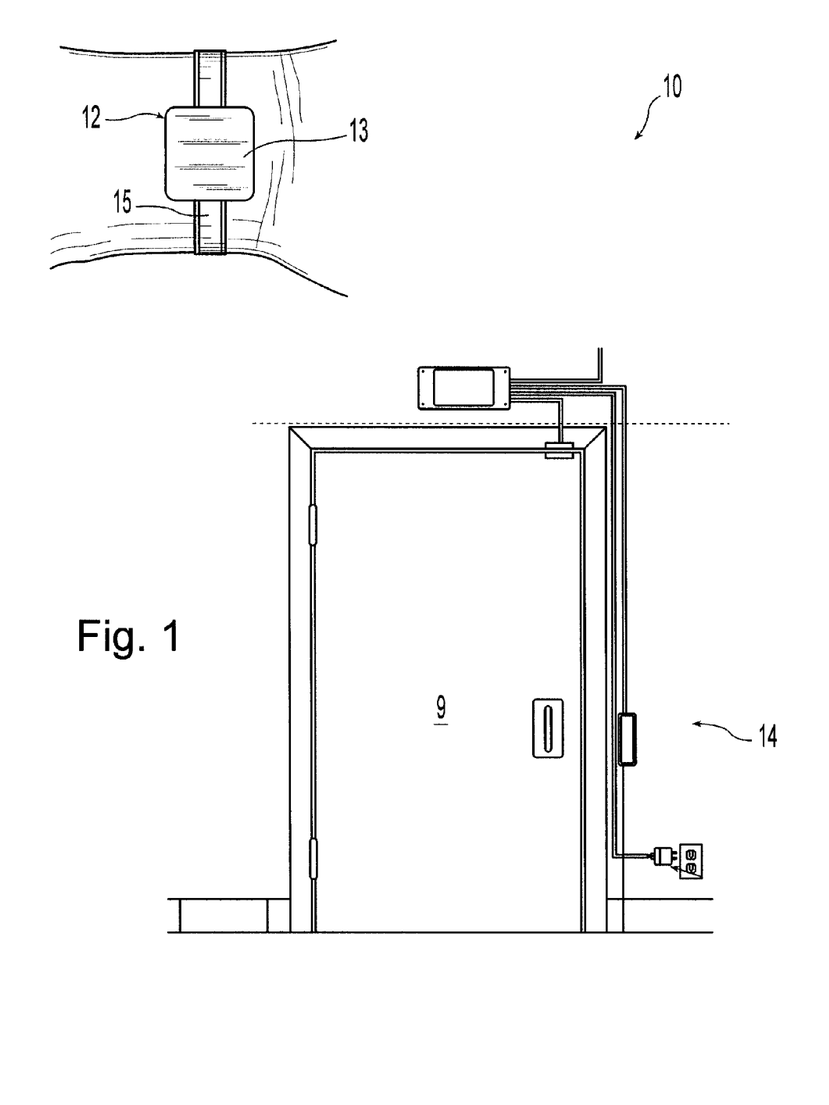
FIG. 1 is view of a patient monitoring system including a signaling device worn by the patient and a door monitor.

As shown in FIG. 1, a patient monitoring system 10 is disclosed to prevent unauthorized patients, such as those suffering from Alzheimer's disease, from leaving an area of a care facility without supervision. Patient monitoring system 10 includes a plurality of signaling devices 12 that are worn by such patients and a plurality of door monitoring units 14. Depending on the configuration of system 10, an alarm will sound if a respective door 9 is opened, as detected by the respective door monitoring unit 14, when a patient wearing a signaling device 12 is too close to the respective door 9. Thus, if a patient wearing a signaling device 12 opens door 9 that they are unauthorized to pass through, an alarm will activate notifying the care providers that an unauthorized patient is attempting to exit an area. Door monitoring unit 14 may activate an audible alarm, visual alarm, and/or may send an alarm signal to a remote location, such as a nurse's station, through wired or wireless communication. According to alternative applications, signaling devices may be placed on medical devices (IV poles, wheel chairs, beds, etc.), other items, and non-patients, such as care providers.

Door monitoring systems 14 may also be equipped with a door lock that locks door 9 when it detects that a patient wearing a signaling device 12 is near the respective door 9. This prevents the patient from opening the respective door 9. Other monitoring units may be provided that detect when a patient is passing through an area, such as a hallway without a door, to detect the location of the patient and signal an alarm. Other monitoring units that interact with signaling devices 12 do not necessarily activate an alarm, but do monitor the location of the patients. Additional details of suitable patient monitoring systems 10 are provided in U.S. Pat. Nos. 4,095, 214; 4,682,155; 5,268,670, the disclosures of which are expressly incorporated by reference herein and U.S. Provisional Patent Application Ser. No. 60/667,178, titled "Patient Monitoring System," filed Mar. 20, 2005, the disclosure of which is expressly incorporated by reference herein.

Signaling device 12 transmits a signal that is detected by door monitoring unit 14. When this signal is detected, door monitoring unit 14 activates the alarm if the respective door 9 is open (and/or locks the respective door 9 with a magnetic, electro-mechanical, or other door lock or monitors the position of the patient without activating an alarm or locking door 9). The signal sent by each signaling device 12 is preferably an electromagnet signal. According to an exemplary embodiment, signaling devices 12 send out a signal at a predetermined frequency within a predetermined tolerance. Door monitoring units 14 are tuned to the predetermined frequency to avoid interference from other sources. According to an exemplary embodiment, each signaling device 12 is tuned to approximately 508 KHz+/−250 Hz. Door monitoring units 14 detect frequencies including this range. Signaling device 12 and door monitoring units 14 may also be tuned to other frequency ranges.

Figure 6:
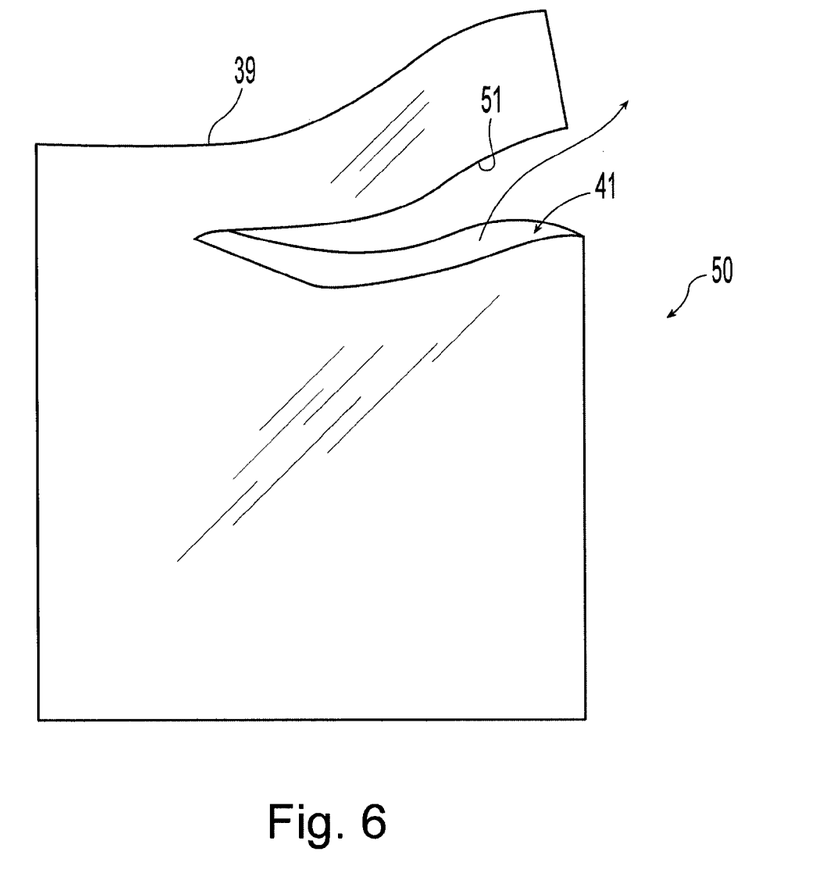
FIG. 6 is a diagrammatic cross-sectional view of the signaling device showing the housing and a circuit board positioned in the housing and a package for storing the signaling device.

As shown in FIG. 6, signaling device 12 includes a circuit board 11 supporting the various electrical components of signaling device 12. Each signaling device 12 further includes a water-tight housing 13 that encloses circuit board 11 and a bracelet or strap 15 that secures housing 13 to a patient's wrist (as shown in FIG. 1), ankle, wheelchair, or other object.

Figure 2:
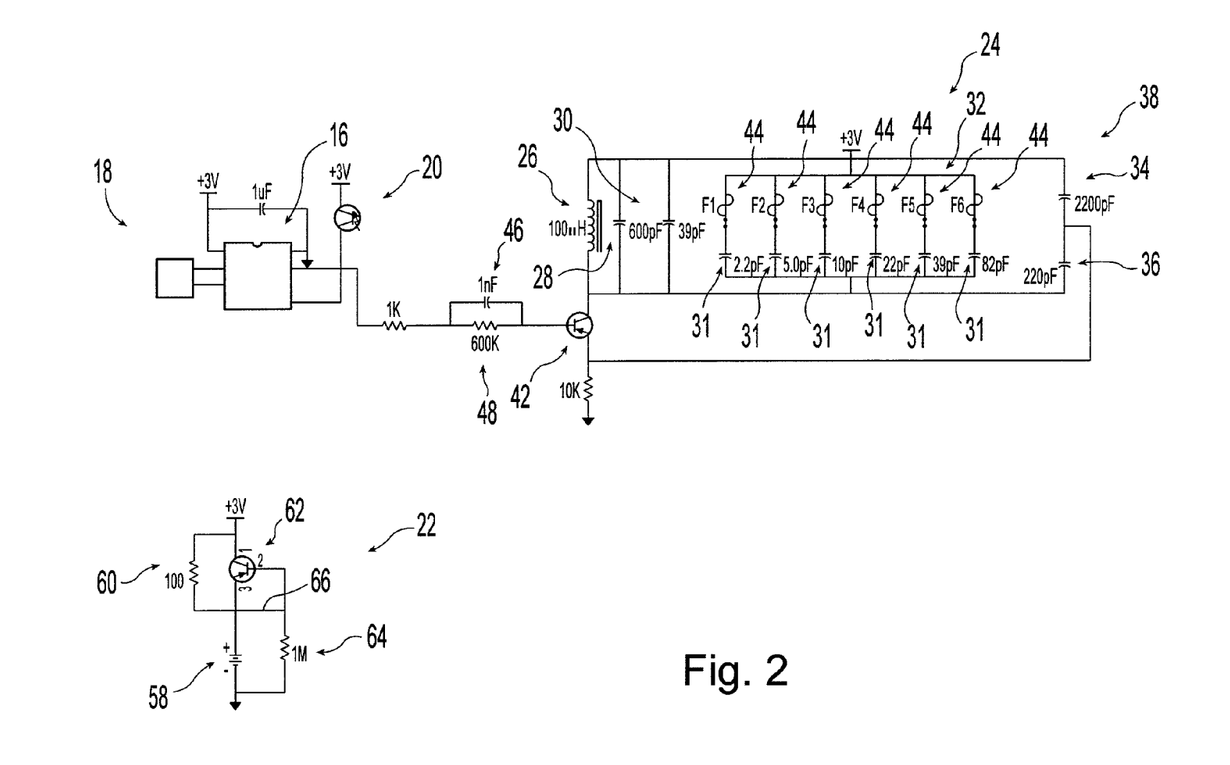
FIG. 2 is diagrammatic view of the circuitry of the signaling device showing the circuitry including a microprocessor, a transmitter or oscillator circuit, an IR detector, a battery circuit, and a clock circuit.

Circuit board 11 supports a microprocessor 16 (as shown in FIG. 2), a timing or clock circuit 18, an IR sensor 20, a battery circuit 22, and an oscillator circuit 24 that generates the predetermined frequency. According to an exemplary embodiment, oscillator circuit 24 is a tank circuit that has a resonant frequency generally dependent on the inductance and capacitance of the components in the circuit. Oscillator circuit 24 includes an inductor 26 that generates the predetermined frequency, two "permanent" capacitors 28, 30, a tuning capacitance array 32 of selected capacitors 31, and a pair of "permanent" capacitors 34, 36 arranged in series. For convenience, capacitors 34, 36 will be referenced as a single capacitor 38. The preferred inductance and capacitance values of the components of oscillator circuit 24 are shown in FIG. 2.

As mentioned above, the resonant frequency (f) of oscillator circuit 24 is a function of the overall inductance and capacitance of oscillator circuit 24.

$$f = \frac{\omega}{2\pi} = \frac{1}{2\pi\sqrt{LC}}$$

As indicated by the above formula, the resonant frequency of oscillator circuit 24 may be adjusted by altering the inductance and/or capacitance of the circuit. According to the exemplary embodiment of the present disclosure, the capacitance of oscillator circuit 24 is adjusted to tune the resonant frequency of oscillator circuit 24 so that is falls within the preferred range (508 KHz+/−250 Hz). According to alternative embodiments, the inductance alone or in combination with the capacitance is adjusted to tune the resonant frequency.

To adjust the capacitance of oscillator circuit 24, one or more of the capacitors 31 in tuning capacitance array 32 is "removed" from circuit 24. By removing a capacitor 31 from circuit 24, the overall capacitance of circuit 24 decreases because of the parallel arrangement of capacitors 31 in oscillator circuit 24. Because the overall capacitance decreases, the resonant frequency of oscillator circuit 24 increases as dictated by the inverse relationship between capacitance and frequency as shown in the above formula.

To "remove" a capacitor 31 in capacitor array 32, a low voltage, high current source is applied to a fuse pad 44 positioned in series with capacitor 31 to be removed so that specific capacitor 31 is no longer in parallel with inductor 26. As shown in FIG. 2, the 82 pF capacitor 31 and 10 pF capacitor 31 have been effectively removed from capacitor array 32, but remain physically attached to circuit board 11. The selection of the 82 pF capacitor 31 and 10 pF capacitor 31 for removal is described in greater detail below. As a result, the "removed" capacitors 31 no longer effect the overall capacitance of oscillator circuit 24. Although fuse pads 44 according to the exemplary embodiment are provided between the positive voltage source and capacitors 31, fuse pads 44 could also be positioned between capacitors 31 and the collector side of tank circuit 24.

According to another embodiment of the present disclosure, an active link, such as BJT or FET transistors, are provided in place of one or more of fuse pads 44. Through use of transistors, capacitors 31 (or inductors as described below) can be actively "removed" or "added" into the array (or series as described below) to raise or lower the resonant frequency.

As shown in FIG. 2, a wide range of capacitors 31 are provided in capacitor array 32 to provide a suitable range of adjustments to the overall capacitance of oscillator circuit 24. Although capacitor array 32 includes six capacitors 31, fewer or more capacitors of lesser or greater capacitance may be provided.

Oscillator circuit 24 is designed so that when all capacitors 31 in capacitance array 32 are in the circuit, the resonant frequency of oscillator circuit 24 is below the preferred range. For example, according to the exemplary embodiment, the calculated resonant frequency is about 485 kHz. However, depending on the actual inductance and capacitance of the components of oscillator circuit 24, the actual resonant frequency will be slightly above or below this value, but in most circumstances will be below the desired resonant frequency range. To test the actual resonant frequency, oscillator circuit 24 is powered up by applying current from microprocessor 16 to a transistor 42. The frequency of the electromagnetic signal is then measured. Assuming that inductor 26 has an inductance at its nominal value plus its tolerance range, the overall capacitance of the system is calculated using an algebraic equivalent of the formula provided above. Next, this capacitance is compared to the desired capacitance of oscillator circuit 24. The desired capacitance is calculated using the algebraic equivalent of the above formula with the desired upper end of the resonant frequency range and the assumed inductance of inductor 26. According to an exemplary embodiment, the desired capacitance is about 980.6 pF.

The difference between the actual capacitance and the desired capacitance is then calculated. Assuming the measured frequency is 485 kHz and the assumed inductance is 1000 uH in an example, the actual capacitance would be about 1073.2 pF and the difference between the desired capacitance and the actual capacitance would be about 92.6 pF. Next, the largest capacitor 31 in capacitor array 32 that is less than this value is selected for "removal" from capacitor array 32 to reduce the overall capacitance of oscillator circuit 24. By selecting a capacitor 31 below 92.6 pF (in this example), overshooting the desired frequency range is avoided. By lowering the capacitance, the resonant frequency of oscillator circuit 24 increases. In the example, the 82 pF capacitor 31 is removed as shown in FIG. 2.

After removal, the overall capacitance of oscillator circuit 24 should be about 991.2 pF resulting in a resonant frequency of about 505.52 kHz. After the adjustment, the resonant frequency of oscillator circuit 24 is again tested. If the resonant frequency is not within the desired range, the actual capacitance is calculated again; compared to the desired capacitance; and the largest remaining capacitor 31 in capacitor array 32 that is less than the difference between the actual and desired capacitance is removed as described above. For example, the 10 pF capacitor 31 in capacitor array 32 would be removed resulting in an overall capacitance of about 981.2 pF and a resonant frequency of 508.08 kHz, which is within the desired range of 508 kHz+/−250 Hz in the exemplary embodiment. If necessary, this process repeats until oscillator circuit 24 is within the desired frequency range.

The capacitance values of capacitors 31 in array 32 are selected to increase by a factor of about two. By providing capacitors 31 in array 32 that increase by a factor of about two, a wide range of overall capacitance values for capacitor array 32 may be achieved by selecting the appropriate combinations of capacitors 31 to remove from array 32. If the capacitance of capacitors 31 increase by exactly a factor of two (i.e. 2.5, 5, 10, 20, 40, and 80 pF), the capacitance of array 32 can be tuned from the lowest capacitance (i.e. 2.5 pF) to the sum of all the capacitances (i.e. 157.5 pF) at increments equal to the lowest capacitance (i.e. 2.5 pF). However, according to the exemplary embodiment, the capacitances increase by about a factor of two (2.2, 5.0, 10, 22, 39, and 82 pF as shown in FIG. 2) because these particular capacitance values are more standard and therefore less expensive. Thus, capacitance values from 2.2 pF to 160.2 pF can be selected for array 32 with incremental differences between 2.2 pF and 4.8 pF.

Figure 3:
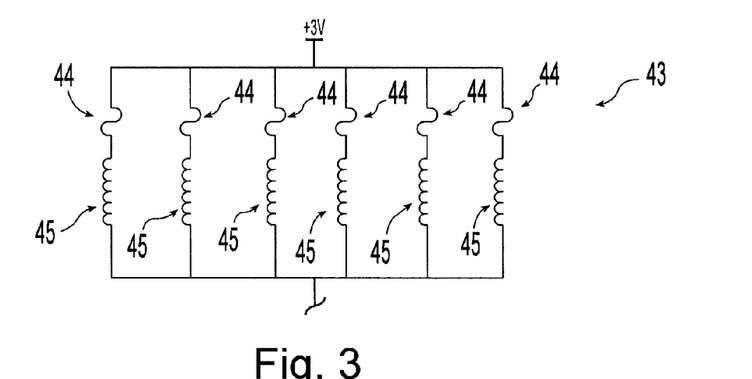
FIG. 3 is a diagrammatic view of an alternative embodiment component of an oscillator circuit.

According to alternative embodiments of the present disclosure, an inductor array 43 as shown in FIG. 3 is provided. In this embodiment, the non-adjusted resonant frequency is selected above the desired range. Inductors 45 in inductor array 43 are selectively removed by exposing selected fuse pads 44 to sufficient current. By removing an inductor 45, the overall inductance of array 43 increases and lowers the resonant frequency of the oscillator circuit. The selection of inductors 45 is similar to that described above for capacitor array 32. Removal of inductors 45 continues until the actual resonant frequency falls within the desired frequency range.

Figure 4:
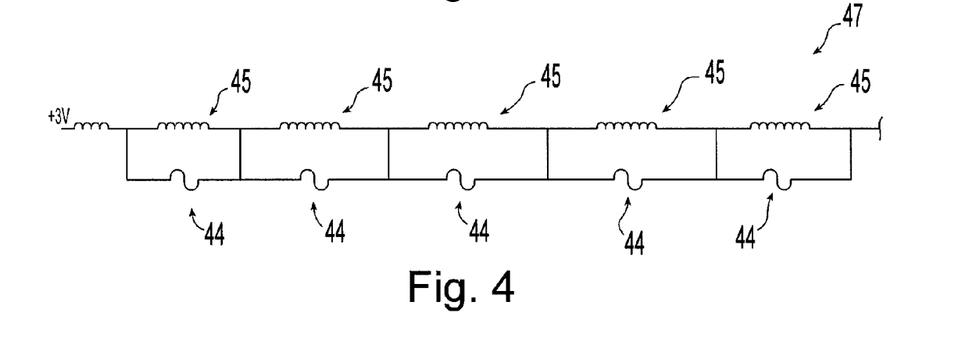
FIG. 4 is a diagrammatic view of another alternative embodiment component of an oscillator circuit.

According to another alternative embodiment of the present disclosure, an inductor series 47 is provided including a plurality of inductors 45 as shown in FIG. 4. In this embodiment, the non-adjusted frequency is selected above the desired range. Inductors 45 are added to the series by exposing selected fuse pads 44 to sufficient current. By adding inductors 45, the overall inductance of series 47 increases and lowers the resonant frequency of the oscillator circuit. The selection of inductors 45 is similar to that described above for capacitor array 32. Addition of inductors 45 continues until the actual resonant frequency falls within the desired frequency range.

Figure 5:
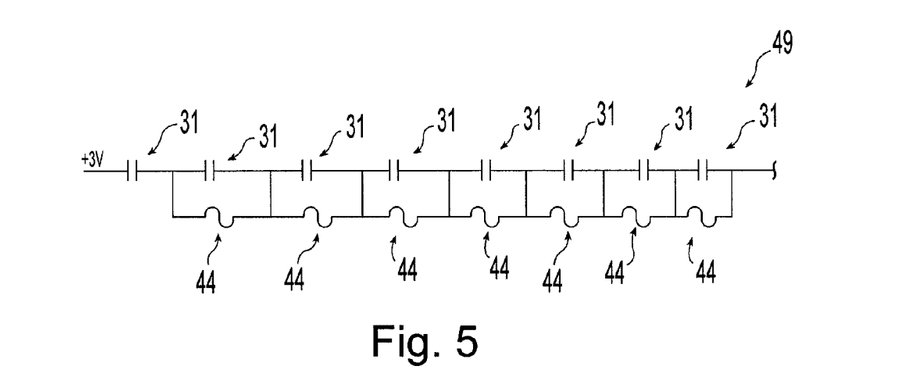
FIG. 5 is a diagrammatic view of another alternative embodiment component of an oscillator circuit.

According to another alternative embodiment of the present disclosure, a capacitor series 49 is provided including a plurality of capacitors 31 as shown in FIG. 5. In this embodiment, the non-adjusted frequency is selected below the desired range. Capacitors 31 are added to the series by exposing selected fuse pads 44 to sufficient current. By adding capacitors 31, the overall capacitance of series 49 decreases and raises the resonant frequency of the oscillator circuit. Addition of capacitors 31 continues until the actual resonant frequency falls within the desired frequency range.

According to yet another embodiment, a selected combination of capacitors and inductors in a circuit are removed or added to raise or lower the resonant frequency. These circuits may include any number and arrangement of capacitor and/or inductor arrays and/or series.

According to other embodiments, fuse pads 44 are replaced with circuit gaps. The circuit gaps are filled to add or remove capacitance or inductance. For example, by replacing fuse pads 44 in FIG. 2 with gaps and filling selected gaps, the overall capacitance of the oscillator circuit increases. Similar circuit gaps may be provided in the series and arrays described herein (including those shown in FIGS. 3-5) and selectively filled to alter the capacitance and/or inductance of the oscillator circuit. According to yet other embodiments of the present disclosure, manually adjustable capacitors and/or adjustable inductors are provided to permit adjustment of the resonate frequency of oscillator circuit 24. Such an adjustable capacitor is described in U.S. Pat. No. 4,682,155.

Microprocessor 16 controls oscillator circuit 24 to provide a modulated signal detected by door monitoring units 14. Microprocessor 16 is programmed in a known manner to provide the modulated signal and other functionality of signaling device 12.

Each signaling device 12 is configured to minimize energy consumption. To conserve energy, signaling device 12 operates in several modes providing different functionality that consumes energy at different rates. Thus, the energy usage of signaling devices 12 is tailored to match the needed functionality of signaling device 12 during different periods of its life cycle. For example, during shipment and storage of signaling device 12, less functionality is required so each signaling device 12 is placed in a mode that reduces energy consumption.

During a typical life cycle, each signaling device 12 may transition through a "production" mode, a "hibernate" mode, a "sleep" mode, a "run" mode, and a "post-run" mode. During production, each signaling device 12 is assembled and provided with a battery 58. With battery 58 installed, each signaling device 12 begins the production mode and undergoes testing and customization as described in greater detail below. The hibernate mode is a transitional mode between the production mode and the sleep mode. During the sleep mode, signaling devices 12 are shipped and stored before use by a patient. After waking up from the sleep mode, signaling devices 12 operate in the run mode during which time they are normally worn by a patient. After the conclusion of the run mode, signaling devices 12 switch to the post run mode and are no longer worn by the patient. According to alternative embodiments of the present disclosure, fewer or more modes may be provided with each signaling device 12.

IR sensor 20 and housing 13 facilitate changing several of the modes of signaling devices 12. As mentioned above, each signaling device 12 includes an IR sensor 20 that is electrically coupled to microprocessor 16. Housing 13 is made of an IR transparent or translucent material that permits IR waves to transmit into an interior 21 of housing 13 that contains IR sensor 20.

Housing 13 is preferably made of an ABS-blended plastic that is IR transparent or translucent so that IR waves are transmitted through housing 13 into interior region 21 that contains IR sensor 20. The exemplary plastic is substantially opaque to visible light. According to alternative embodiments of the present disclosure, other materials or configurations are provided to permit IR waves to penetrate through housing 13 to IR sensor 20. For example, according to another embodiment, a clear plastic housing is provided. According to another embodiment, an IR transparent or translucent window is provided in an otherwise IR opaque material to permit IR waves to reach IR sensor 20.

As shown in FIG. 6, housing 13 includes a base or tub 50 that defines interior region 21 of housing 13 and an opening 54 into housing 13 that receives circuit board 11 and the components mounted thereon. Housing further includes a cover 56 that is received in opening 54 and heat welded to base 50 to form a liquid-proof enclosure for circuit board 11 and the components mounted thereto.

Because IR waves transmit through housing 13, the liquid proof integrity of housing 13 is not impacted. Thus, signaling devices 12 can be provided with a change of mode feature without negatively impacting the integrity of housing 13. According to alternative embodiments of the present disclosure, other techniques for providing a non-intrusive change of mode feature are provided. For example, microprocessor 16 changes modes of signaling device 12 from the hibernate mode to the sleep mode and from the run mode to the post run mode as discussed below. According to other embodiments, stimuli other than IR waves are used, such as visible light, radio waves, or other waves having other wave lengths used in conjunction with an appropriate sensor. According to another embodiment, each signaling device is provided with a reed switch inside the housing that separate the microprocessor from a voltage source. A user passes a magnet over the housing to move the position of the reed switch to expose the microprocessor to the voltage source and activate the microprocessor. According to another embodiment, an inductor is provided in the housing and a magnet is passed over the housing to induce a current in the inductor. The microprocessor detects the current and changes mode. According to another embodiment, the housing is provided with a flexible portion and a dome or other switch is provided under the flexible portion. A user presses the flexible portion to move the switch and activate the microprocessor.

Each of these embodiments provides a non-intrusive means for actively changing the mode of the signaling device. In the exemplary embodiment, signaling device 12 actively changes from the sleep mode to the run mode. The non-intrusive means avoids compromising the waterproof integrity of the housing because no force transmission object, such as a plunger or pin, penetrates the housing through an opening in the housing. This avoids the need for seals around a plunger, pin, or other intrusive means. Although the exemplary embodiment includes a non-intrusive means for actively changing the mode of signaling device 12, intrusive means, such as a plunger or pin that passes through an opening in the housing may also be used with signaling devices including the other features described herein.

Before insertion into housing 13, circuit board 11 is assembled and provided with battery 58. Once battery 58 is installed, signaling device 12 begins operating in the production mode and IR sensor 20 is activated. With battery 58 installed, the frequency of oscillator circuit 24 is tuned as described above. Then, circuit board 11 is inserted into interior region 21 of base 50 and cover 56 is heat welded to base 50 to seal circuit board 11 in interior region 21.

After final assembly (including sealing of housing 13), an IR test code is sent to signaling device 12 and received by IR sensor 20. The IR test code is detected by microprocessor 16, which energizes oscillator circuit 24 in response to the IR test code. An external test apparatus (not shown) is then used to detect the carrier frequency and signal strength of the emitted signal to determine if they fall within acceptable ranges after full assembly.

Near this same time, each signaling device 12 is programmed through IR sensor 20 to perform certain features to provide different signal device versions while using the same base signaling device 12. For example, for one version an IR programming code may be sent to a signaling device 12 instructing it to send an un-modulated signal with no data and for another version an IR programming code may be sent to another signaling device 12 instructing it to send a modulated signal with data. According to other embodiments, the use period may be sent for different lengths depending on end user preference (ex. 30 days, 90 days, etc.). Each signaling device 12 may also be pre-programmed with a unique ID before storage and shipment. Each pre-programmed ID is indicated on a package 50 or otherwise. At the care facility, the care provider can then select from a collection of signaling devices 12 based on the unique ID provided on package 50. Thus, after assembly, multiple signaling device versions can be provided to various care facilities that all use the same base signaling device 12.

After successfully passing the signal test, an IR hibernate code is sent to signaling device 12 and received by IR sensor 20. The IR hibernate code is detected by microprocessor 16, which places signaling device 12 into the hibernate mode that temporarily disables IR sensor 20 by turning the pin to IR sensor 20 to high. Because IR sensor 20 is disabled, it no longer responds to IR waves, whether coded or from ambient sources.

During this temporary hibernation period, signaling device 12 is placed in package 50 and package 50 is sealed. After a predetermined period of time, microprocessor 16 changes to the sleep mode. According to an exemplary embodiment, the predetermined time is about 2 hours.

According to one exemplary embodiment of the present disclosure, each signaling device 12 remains the sleep mode during storage at the device manufacturer, during shipment from the device manufacturer to a care facility, and during storage at the care facility. When it is time to use each respective signaling device 12, it transitions from the sleep mode to the run mode as described in greater detail below.

While in the sleep mode, microprocessor 16 and the other components of signaling device are powered down so that little or no battery power is consumed, but IR sensor 20 is active. If IR sensor 20 detects sufficient IR waves, it activates microprocessor 16 to transition signaling device 12 from the sleep mode to the run mode as described in greater detail below.

As mentioned above, each signaling device 12 is shipped in package 50. Package 50 is made of an IR blocking material. When signaling device 12 is positioned in package 50, it blocks IR waves from reaching signaling device 12 so that signaling device 12 does not change modes and remains in sleep mode. Thus, during shipment and storage of signaling device 12, little battery power is consumed to prolong the useful life of each signaling device 12.

Before signaling device 12 is positioned in pouch 50 for storage and shipment, one edge or end 39 is left unsealed and open. The other edges are preferably sealed and closed. After assembly and testing, each signaling device 12 is positioned in an individual pouch 50 through open end 39. According to one exemplary embodiment of the present disclosure, package 50 is a bag or pouch made of aluminum foil coated with Mylar®-brand plastic.

After signaling device 12 is positioned in pouch 50 through open end 39, open end 39 is heat sealed by melting the Mylar®-brand plastic film to block contaminants from entering interior 41 of pouch 50. The aluminum foil of pouch 50 blocks IR waves from penetrating interior 41 of pouch 50 so that IR sensor 20 is not excited and signaling device 12 does not change state. Because pouch 50 shields signaling device 12 before being opened for use, signaling device 12 remains in the sleep mode during shipment and storage at the care facility.

According to other embodiments of the present disclosure, other IR blocking materials are used to store signaling devices 12, such as a black plastic pouch or any other materials that are IR opaque. Exemplary pouch 50 encloses all of signaling device 12 during shipment and storage to block IR waves from reaching IR sensor 20. However, according to other embodiments, other IR blocking configurations are provided that cover only portions of signaling device 12 to block IR waves from reaching IR sensor 20.

To open pouch 50, a care provider tears it open, as shown in FIG. 6, to permit access to interior 41 and expose signaling device 12 to ambient IR waves that enter through tear 51. If sufficient IR waves do not penetrate through tear 51 to change the mode of signaling device 12, it will also be exposed to ambient IR waves after removal from interior 41. Thus, when pouch 50 is opened (or when signaling device 12 is removed from pouch 50), signaling device 12 changes mode without the care provider having to proactively change the mode of signaling device 12.

When package 50 is opened and/or signaling device 12 is removed from package 50, IR sensor 20 is exposed to sufficient ambient IR waves present in the environment outside of package 50 that transmits through housing 13. In response to being exposed to the IR waves, IR sensor 20 creates a voltage signal that is detected by microprocessor 16, which changes signaling device 12 from the sleep mode to the run mode. Thus, according to one exemplary embodiment of the present disclosure, ambient IR waves are used to change the mode of each signaling device 12 after a care provider opens package 50. Upon opening of package 50, as shown in FIG. 6, signaling device 12 automatically changes from the sleep mode to the run mode.

By providing this automatic change of mode, no extra step is required by the care provider to activate signaling device 12. Furthermore, no tools are required to activate signaling devices 12 according to the exemplary embodiment. Although signaling device 12 changes state in response to ambient IR waves, other stimuli can be detected to automatically change the state of signaling device. For example, according to an alternative embodiment of the present disclosure, a change in pressure is detected to change the state of the signaling device. The signaling device may be vacuum packed. When the package is opened, an electronic pressure sensor detects the positive change in pressure to automatically change the state of the signaling device.

According to another embodiment, coded IR waves may be used to change the mode of signaling device 12. Such coded IR waves may be provided by an IR emitting device (not shown) provided to each care facility. Technology similar to that provided in TV remote controls and other IR wave emitters could be used to transmit the coded IR wave.

As discussed above, once package 50 is opened, ambient IR waves pass through housing 13 and excite IR sensor 20, which creates voltage in response to the IR waves. This voltage activates microprocessor 16, which removes signaling device 12 from the sleep mode and places it in the run mode.

In the run mode, microprocessor 16 controls the operation of oscillator circuit 24 so that it sends out the modulated carrier frequency. Embedded within the carrier frequency is a default signaling device ID. For a predetermined time period after switching from the sleep mode to the nm mode, IR sensor 20 remains enabled to permit programming of signaling device 12. After this time, microprocessor disables IR sensor 20 to conserve power.

During this predetermined time when IR sensor 20 remains enabled, a care provider may change the factory programmed default ID associated with signaling device 12 to a new or unique ID associated with a particular patient, other person, piece of medical equipment, or other item. During this time, signaling device 12 may also be programmed with other information, such as patient specific information. Such information may include a patient's room and/or floor number, a patient's medical condition (i.e. diabetic, allergies, etc.), or other information specific to the patient. According to the exemplary embodiment of the present disclosure, IR sensor 20 remains enabled for 30 minutes after switching from the sleep mode to the run mode before being disabled by microprocessor 16.

During this time, an IR emitting programming device located at the care facility may be loaded with a new or unique ID to transmit the ID to signaling device 12. Because each signaling device 12 can be programmed with its own unique ID, each patient's movements can be monitored and recorded with a single ID used on successive signaling devices 12. For example, after a signaling device 12 with a unique ID transitions to the post run mode or otherwise goes out of service, that same unique ID can be programmed into a new signaling device 12 for use with the same patient. The IR emitting programming device may also include an RF transceiver that detects the unique ID of a signaling device 12 during the run mode or when signaling device 12 is prompted to transmit the unique ID during the post run mode. With this unique ID, the IR emitting programming device would then load the unique ID into a new signaling device 12 so that a care provider would not need to manually load the unique ID into the IR emitting device. After signaling device 12 is programmed with a unique ID, microprocessor 16 disables IR sensor 20 to conserve power regardless of whether 30 minutes has passed. The IR emitting programming device may be configured to remain at one location or may be a handheld portable unit, similar to a TV remote control.

For a predetermined run time, signaling device 12 operates in the run mode and transmits the modulated carrier frequency that includes the signaling device ID. As described above, door monitors 14 detect this signal to determine the proximity of the wearer of the respective signaling device 12 relative to the respective door 9. During the run mode, microprocessor 16 switches signaling device 12 from a normal period to a replacement period. As a result of the switch, signaling device 12 indicates that the end of the run mode is approaching and it is necessary to replace signaling device 12 or in the near future. This indication may be provided in any manner, a few of which are described in greater detail below.

During the majority of the run mode of the exemplary embodiment, signaling device 12 operates in the normal period of the run mode and signaling device 12 transmits the modulated carrier frequency in a manner indicating that it is in the normal period. Near the end of the run mode, signaling device 12 switches to operate in the replacement period of the run mode and continues to transmit the modulated carrier frequency. However, while in the replacement period, the modulated carrier frequency indicates that the respective signaling device 12 is in the replacement period. The indication provided in the modulated carrier frequency for either period may be the presence of a particular piece of data, the absence of a particular piece of data, a change in a particular piece of data, or any other way of communicating the period status.

Door monitoring units 14 are configured to detect the change of period of the respective signaling devices 12 by detecting the indicator in the modulated carrier frequency or otherwise. As a result, the respective door monitoring unit 14 indicates that the respective signaling device 12 needs replaced. Door monitoring units 14 may provide a visual text message or other visual indication that a detected signaling device 12 needs replaced or may provide any other type of indicator, such as an audible announcement. During the indication, door monitoring unit 14 may identify the respective signaling device 12 by its ID or otherwise indicate which signaling device 12 needs replace by providing an identifier, such as the patient's name.

In addition to door monitoring units 14, other devices may be provided that can detect the period in which signaling devices are operating. For example, the IR emitting programming device may detect the period of a particular signaling device 12 and provide an indication of the period, such as a green light for the normal period and a red light for the replacement period.

Door monitoring units 14 or other detectors may also send an indication to a remote location, such as a nurse call center, that a respective signaling device 12 needs replaced. This indicator may include the device ID, patient name, or other identifier. Each respective signaling device 12 may also have an indicator, such as an LED, that indicates that it is in need of replacement or otherwise is no longer in the normal period.

According to an exemplary embodiment of the present disclosure, the normal period of the predetermined run time is 90 days and the replacement period is 3 days. Thus, for 3 days, each signaling device 12 indicates that it needs replaced. According to other alternative embodiments of the present disclosure, the predetermined run time may be other periods of time such as 7 days, one year, or other periods of time with appropriate normal periods and replacement periods.

After this replacement period of the run mode, microprocessor 16 switches to the post run mode. During the transition, microprocessor turns off oscillator circuit 24 and enables IR sensor 20. If the care provider needs to retrieve the ID of the respective signaling device 12 while in the post run mode, they can send an IR request code to the respective signaling device 12. In response to receiving the request code, microprocessor 16 energizes oscillator circuit 24 that transmits the unique ID code through the modulated carrier frequency. After a predetermined time, microprocessor 16 turns off oscillator circuit 24 and IR sensor 20 remains enabled to receive additional instructions. According to the exemplary embodiment, the IR sensor 20 remains enabled until battery circuit 22 runs out of power.

As shown in FIG. 2, battery circuit 22 includes battery 58. In a first exemplary configuration, battery circuit 22 includes a 100 Ohm resistor 60. Transistor 62 and 1 MOhm resistor 64 are not provided in the first exemplary configuration. To test the strength of battery 58, the voltage drop over resistor 60 is measured at test points to determine the current and battery strength.

In a second exemplary configuration, battery circuit 22 includes transistor 62 and resistor 64, but does not include resistor 60. To enable the transmission of current from battery 58 to the remainder of circuit 24, link 66 is evaporated or otherwise blown out. With link 66 removed, current travels through the base of transistor 62 and transistor 62 permits current to flow to the remainder of circuit 24. With link 66 in place, transistor 62 blocks the current flow. Thus, to conserve battery power, link 66 may be left in place until signaling device 12 is ready for final assembly.

Clock circuit 18, shown in FIG. 2, includes a timer that is either internal to microprocessor 16 or external to microprocessor 16. Microprocessor 16 uses the output frequency of the clock circuit 18 as a clock signal for a clock function to determine when the predetermined times discussed above have expired.

In addition to or as an alternative to IR sensor 20, signaling device 12 may be configured to receive RF signals from various sources to change modes or otherwise interact with other devices. When exposed to RF waves, inductor 26 will produce a signal indicative of the RF wave. Microprocessor 16 can be programmed to recognize this signal and decode any information provided in the signal. Based on detecting an RF signal and/or information provided in the signal, microprocessor 16 may change the mode of signaling device 12 (as discussed above with respect to IR sensor 20 or otherwise) or otherwise respond to receiving the RF signal.

According to one application, door monitoring units 14 and signaling devices 12 are both provided with RF transceivers. Microprocessors 16 of signaling devices 12 are programmed to respond to RF signals sent from door monitoring units 14. In one example, the RF transmission by door monitoring units 14 is used to conserve battery power. When microprocessor 16 of signaling device 12 no longer detects an RF signal from door monitoring units 14, microprocessor 16 powers down oscillator circuit 24 so that it no longer transmits a signal and conserves battery power. In an example, microprocessor 16 will stop detecting the RF signal at about 10 feet from the respect door monitoring unit 14. In the present example, the distance at which door monitoring units 14 lock the respective doors 9 based on detecting a signaling device 12 is preferable less than 10 feet, such as 4 feet. Microprocessor 16 may determine the distance from door monitoring units 14 by determining the RF signal strength or otherwise. Thus, while the patient is 10 feet or more away from door monitoring units 14, it conserves battery power by not transmitting a signal itself. Once microprocessor 16 detects that it is again within 10 feet from a door monitoring unit 14 based on the signal received from inductor 26, it will start sending a signal again using oscillator circuit 24 as described above so that door monitoring units 14 can detect the proximity of the patient wearing the respective signaling device 12. In addition to turning oscillator circuit 24 on and off, door monitoring units 14 may also change other modes of signaling devices 12.

Patient monitoring system 10 includes multiple features that may be provided with or without the other features. For example, signaling devices 12 may or may not include features that provide functionality in their own right. Exemplary independent features include, but are not limited to, capacitor array 32 (and the other signal adjustment means described herein); IR sensor 20 (and other incoming communications means described herein); a microprocessor 16 that is programmed to receive incoming communications through IR sensor 20 or otherwise; wave opaque package 50; and any other such features disclosed herein.

The invention claimed is:

1. A signaling device assembly including
a package including an interior region, and
a signaling device for use with a personal monitoring system that detects the location of a person wearing the signaling device, the signaling device being positioned in the interior region of the package, the signaling device including a housing, a control circuit, and non-intrusive means for changing the mode of the control circuit, wherein the housing is devoid of seals.

2. The assembly of claim 1, wherein the non-intrusive changing means includes a wave sensor configured to detect a wave and the package substantially blocks the wave.

3. The assembly of claim 2, wherein the wave sensor is an IR sensor and the package blocks IR waves.

4. The assembly of claim 2, wherein the wave sensor receives predetermined commands to program the control circuit.

5. The assembly of claim 2, wherein the housing is opaque to the wave.

6. A method of enabling a signaling device for use with a personal monitoring system that detects the location of a person wearing the signaling device, the method including the steps of
providing a signaling device configured to communicate with the personal monitoring system, the signaling device having a sleep mode and an active mode, and
automatically changing the mode of the signaling device from the sleep mode to the active mode to enable the signaling device, wherein the signaling device is positioned in a package and the automatically changing step occurs after the package is opened.

7. The method of claim 6, wherein the step of automatically changing the mode of the signaling device from the sleep mode to the active mode is triggered by waves being detected by a wave sensor of the signaling device.

8. The method of claim 6, further comprising the step of automatically changing the mode of the signaling device from the active mode to the sleep mode while the signaling device is positioned in the package.

9. The method of claim 6, wherein the signaling device includes a strap, further comprising the step of coupling the housing to a patient with the strap.

10. A signaling device assembly including a package including an interior region, a signaling device for use with a personal monitoring system that detects the location of a person wearing the signaling device, the signaling device being positioned in the interior region of the package, the signaling device including a housing, a control circuit, and non-intrusive means for changing the mode of the control circuit, the control circuit is supported by the housing, and a communicator supported by the housing and configured to communicate with the personal monitoring system, the control circuit monitors a predetermined useful life of the signaling device and instructs the communicator to send a signal indicating the end of the useful life is approaching, wherein the predetermined useful life is 90 days.

11. The assembly of claim 9, wherein the control circuit instructs the communicator to send the signal at a predetermined time before the end of the predetermined useful life of the signaling device.

12. The assembly of claim 9, wherein the control device continues to instruct the communicator to send the signal until the predetermined useful life ends.

13. A signaling device assembly including a package including an interior region, a signaling device for use with a personal monitoring system that detects the location of a person wearing the signaling device, the signaling device being positioned in the interior region of the package, the signaling device including a housing, a control circuit, and non-intrusive means for changing the mode of the control circuit, the control circuit is supported by the housing, and a communicator supported by the housing and configured to communicate with the personal monitoring system, the control circuit monitors a predetermined useful life of the signaling device and instructs the communicator to send a signal indicating the end of the useful life is approaching, wherein the predetermined useful life begins automatically after the package is opened.

* * * * *